United States Patent [19]

Kaartinen

[11] 4,269,212
[45] May 26, 1981

[54] PROCEDURE AND APPARATUS FOR MANIPULATING BATCHES OF LIQUIDS

[76] Inventor: Niilo Kaartinen, Vuolahti, 21620 Kuusisto, Finland

[21] Appl. No.: 28,510

[22] Filed: Apr. 9, 1979

[30] Foreign Application Priority Data

Apr. 10, 1978 [FI] Finland .............................. 781090
Sep. 14, 1978 [FI] Finland .............................. 782829

[51] Int. Cl.³ .............................................. F17D 1/18
[52] U.S. Cl. .................................... 137/13; 137/341; 137/606; 137/861; 137/884
[58] Field of Search ................. 137/341, 13, 606, 884, 137/883, 861; 62/293; 165/96

[56] References Cited

U.S. PATENT DOCUMENTS

| | | | |
|---|---|---|---|
| 1,874,787 | 8/1932 | Mogridge | 137/341 X |
| 3,055,055 | 9/1962 | Cook et al. | 137/341 X |
| 3,398,262 | 8/1968 | Kahn | 137/341 X |
| 3,457,943 | 7/1969 | Kawabata | 137/884 X |
| 3,820,352 | 6/1974 | Mahler | 62/293 |
| 4,082,109 | 4/1978 | Sun et al. | 137/340 |

*Primary Examiner*—William E. Tapolcai, Jr.

*Attorney, Agent, or Firm*—Haseltine and Lake

[57] ABSTRACT

The application discloses a procedure appropriate in the manipulation especially of small batches of liquid and an apparatus for carrying out the procedure, these being based on the use of valves closable by freezing and openable with the aid of electrical heating elements. The apparatus comprises an integral system composed of volumes and of conduits connecting these, wherein the conduits have been provided with said freezable valves. The transfer of liquids within the sytem is accomplished by means of control signals directed to the valve heating elements. As valve heating elements film resistances incorporated in plate-like components are employed in such manner that one component establishes a plurality of valves. At the same time these valves are connected to a common refrigerator. The components afford the possibility to incorporate in the apparatus a great number of closable appropriate for the storage and treatment of batches of liquid, whereby the apparatus may be employed in the capacity of an electronically controllable device for analysis, determination and identification operating without moving mechanical parts.

12 Claims, 8 Drawing Figures

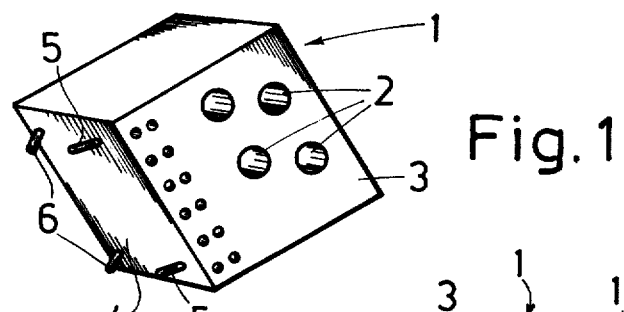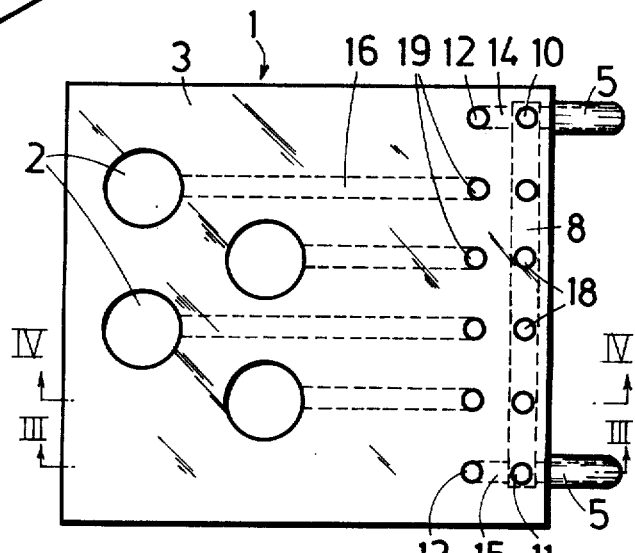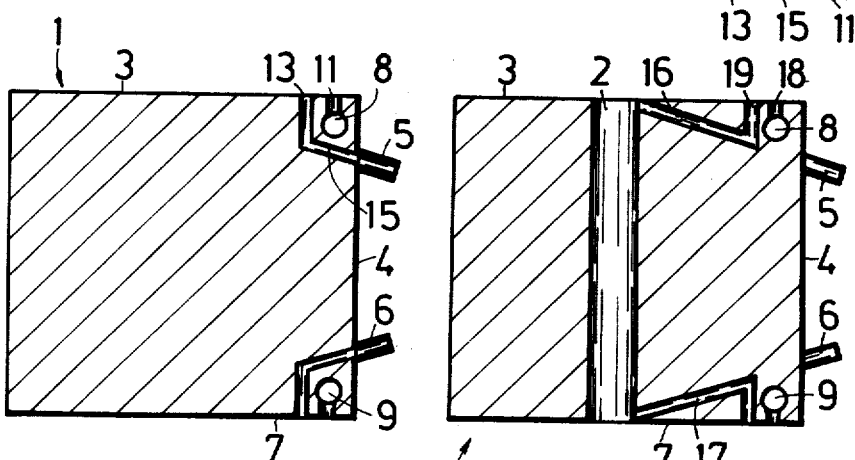

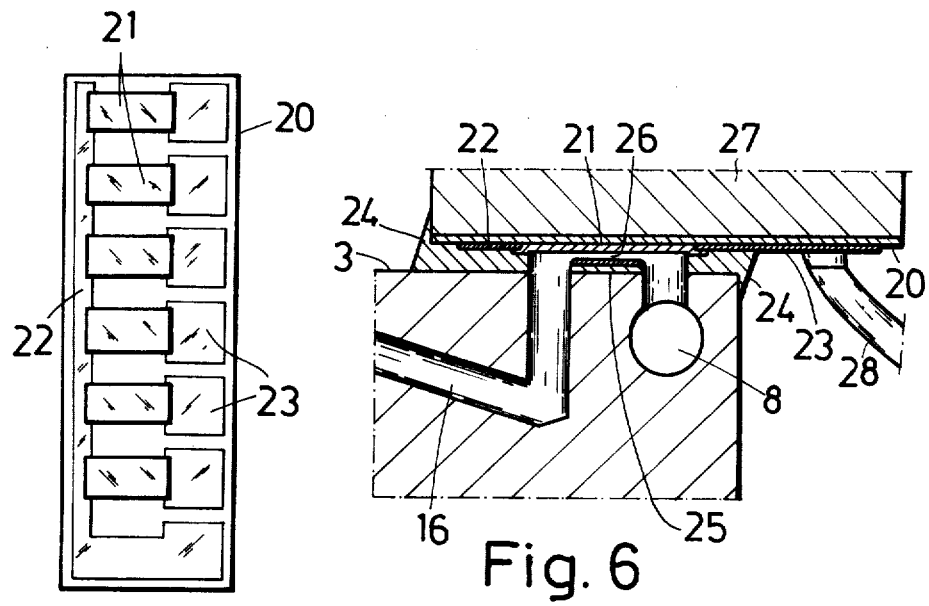
Fig. 5
Fig. 6
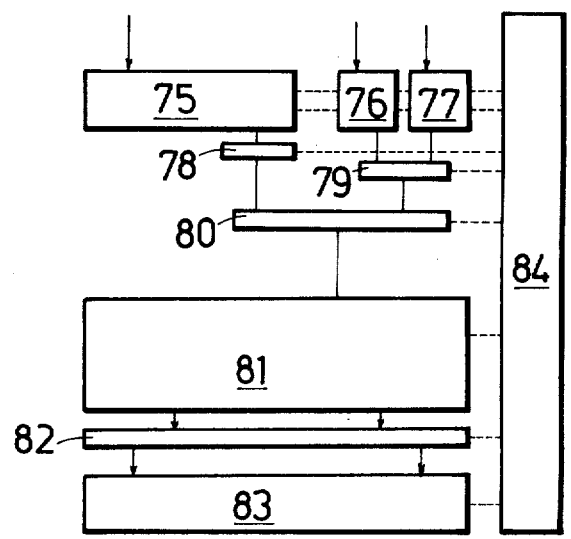
Fig. 8

PROCEDURE AND APPARATUS FOR MANIPULATING BATCHES OF LIQUIDS

The present invention concerns a procedure for use in manipulating batches of liquids, wherein liquid is transferred along a conduit from one volume to another with the aid of differential pressure and wherein breaking of the flow path is accomplished by cooling the conduti so that it will be shut as the liquid within the conduit freezes.

Control of liquid flow in a conduit is usually by means of valves, stopcocks and other similar closing means. Conventional closing means are manually operated or mechanically acting and they comprise moving parts which plug the liquid flow path. However, such closing means have the drawback that sealing difficulties are caused by the gaps remaining between components. Moreover, the liquid penetrating into the gaps makes it harder to keep the valve clean: this has its significance particularly when different liquids have to be conducted through one valve.

The said drawbacks have been avoided in those valves which base their operation on the freezing of the liquid within the conduit, at the valve point. Valves of this type, which have no moving parts whatsoever in contact with the liquid that is being handled, have been developed for the special needs of certain process industries. The cooling of the liquid is accomplished in these valves by the aid of a cooler located outside the conduit and which may operate with a suitable refrigerating substance, for instance. The use of these valves is however limited by the fact that they are big and awkward to use and, in addition, their operation is comparatively slow.

The object of the present invention is to set up a procedure based on the use of valve closing by freezing and with the aid of which batches of liquids can be efficiently manipulated without the drawbacks presented. The invention is characterized in that batches of liquid are manipulated in a system consisting of storage or treatment volumes and of conduits connecting these, where the conduit between two given volumes comprises at least one valve point communicating with a refrigerator, the conduit being freezable to be closed at this point, and which has furthermore been fitted with an electrically controlled heating element by the aid of which the valve may be opened by raising its temperature to be higher than the freezing point of the liquid; that the directing of a batch of liquid into a given volume of the system is accomplished by controlling the valves on the flow route of the liquid to be open; and that enclosing of the liquid in said volume is accomplished by switching off the heating of the valves in the conduits adjoining on the volume in question, whereby the liquid can freeze at the said valves. The providing of the valve with an electrically controllable heating element enables the refrigerator to be kept operating continuously. Opening and closing of the valve is simply accomplished with the aid of an electrical control signal, and the functioning of the valve is renderer highly reliable thereby. Moreover, the freezing of the liquid in the valve after the heating has been taken off is very fast because the surroundings of the valve are already refrigerated. Since in the procedure of the invention the manipulation of batches of liquid is substantially based on the closing and opening of valves in the conduits, the electrical control of the valve actions enables the functioning of the manipulation system to be automated.

The transfer of a batch of liquid from one volume to another is accomplished in the procedure of the invention with advantage in that the transfer route consisting of conduits and/or volumes is arranged at first to be at least partly empty of liquid and then as liquid is being transferred the liquid flow is disrupted by freezing in advance the valve at the shut-off point, whereby the liquid arriving at the valve will immediately freeze and close the conduit. Such a valve, which cuts off the liquid flow that reaches it, shall be so designed that the flow velocity of the liquid is efficiently lowered therein. It must at the same time be so narrow in one dimension at least that its through-and-through freezing takes place instantaneously. For instance in the manipulation of water-based liquids the smallest dimension of the valve should as a rule be less than 0.5 mm, and it is most advantageous to use valves with a smallest dimension between 0.05 and 0.1 mm. Differing from standard valves, a narrow valve of this type has three functional states: it is either fully open when the heating element is in operation or open for gas flow only when the heating is shut off, or fully closed when the liquid has frozen in the valve. A narrow valve has the further advantages of low energy consumption, minimal dead space and small size, all of which make it particularly well suited for the manipulating of small liquid batches. It should be noted however, that in a liquid manipulation system according to the present invention all valves must by no means be such dynamically closing valves as have just been described: their use may be confined to those points where rapid cut-off of the liquid flow is desired.

A basic operation in the procedure of the invention is the dispensing of a batch of liquid of given size into any one of the volumes belonging to the system and, thereafter, its transportation forward in the system. This is done, for instance, when the liquid is being mixed in a given proportion with another liquid. In that case the second liquid is used for transporting the dispensed liquid quantity by letting it push the liquid quantity ahead of itself from the dispensing volume to a mixing volume located later in the system. However, the straightforward accomplishment of these operations involves a number of sources of error, which may introduce inaccuracies in the quantitative manipulation of liquids. Since the procedure of the invention is particularly well suited for the manipulation of very small liquid quantities, the cross section areas of the conduits employed in the system approach capillar dimensions, and as a result liquid residues will form by the effect of capillary forces, on concave surfaces of the conduits in particular. These reduce the volume of the liquid batch next to be transported along the same conduit and thereby lead to incorrect dosage. The liquid residue may furthermore contains a dissolved component at very high concentration and which will cause a high error when it is admixed with the following batch of liquid where the content of this component is low. Errors may also be introduced by the circumstance that some of the liquids being manipulated undergo permanent changes as they freeze in the valves in the conduits. When these valves are later opened, these particular liquid quantities, which may possibly have deteriorated to be unusable, will be entrained and carried along to the subsequent treatment steps. But all these potential sources of error can be avoided if one accomplishes the dispensing of the liquid batch in the system into a first volume and its transfer through a connecting conduit into another volume located later in the system through an input conduit connected with said first volume and driven by the flow, by filling the input conduit and the connecting conduit and the first volume therebetween, to being with, with an auxiliary liquid and closing the valves in the input and connecting conduits, thereafter voiding the said first volume of auxiliary liquid through auxiliary conduits fitted with valves, filling it with the liquid to be dispensed and closing the valves in the auxiliary conduits, and finally opening the valves in the input and connecting conduits, whereby the liquid batch that has been dispensed into said first volume is transferred into said second volume.

The avoidance of errors in a dispensing process according to the procedure described is essentially based on the use of an auxiliary liquid and of auxiliary conduits connected to the line constituted by the input and connecting conduits. For instance, errors due to liquid residues are avoided in that the volume used for dispensing can be cleaned and dried through the auxiliary conduits prior to the dispensing step.

Drying may be further speeded up by flushing, to start with, the volume with a volatile liquid, which is then evaporated with the aid of gas flow. The cleaning and drying of the volume, as well as its filling with the liquid batch to be dispensed, may be carried out completely independent of what is happening simultaneously in other parts of the system. The manipulation actions are considerably speeded up hereby. The liquid batch to be dispensed is introduced into the volume after the drying phase through said auxiliary conduits, and the valve in the conduit serving as exit path will close after filling of the volume dynamically. The variations which may possibly occur in the degree of filling of this valve, as well as potential deterioration of the frozen liquid, are devoid of significance because the liquid frozen in the valves is no longer included in the further treatment of the liquid batch. For the auxiliary liquid, again, one may select a suitable anti-freeze liquid, and it is particularly advantageous to use as auxiliary liquid a solvent which is a component in the liquid batch to be dispensed, whereby admixture of the auxiliary liquid to the liquid batch causes no detriment.

In order that the manipulating of liquids in the system might be completely controlled, it is advantageous to monitor the transfer of the liquid batch by means of a mechanism which is independent of the operation of the valves. Such a mechanism may consist of a flow or differential pressure measuring circuit connected to the conduits, which may be carried out e.g. with the aid of pressure-sensitive piezoresistive elements mounted in the conduits. On the basis of the signals from such a measuring circuit the progress of the liquid batch in the system may be observed and one may make sure of its arrival at its destination before one goes over to the next manipulation step.

The monitoring of the manipulation system may be further enhanced by observing the operation of the individual valves by the aid of operational state measuring circuits connected to them. When this is done, while at the same time the transfer of liquids is monitored as described, one obtains continuous information of what is taking place at any moment in each part of the system, and any disturbances that may develop are thus immediately observable.

It is advantageous in view of controlling the system as well as its supervision to use as heating elements in the valves, electric resistances. Cooling of the conduit for closure is effected by interrupting the electric current passing through the resistance. If the resistance is made of thermistor compound, one may in the monitoring of the valve action make use of the resistor's thermistor characteristic; the monitoring is then in practice effected by observing the change of resistance of the resistor with the aid of such a low voltage which has no substantial effect on the temperature of the valve itself. It is also possible, on the other hand, to provide the valves with separate sensor elements, which furnish information regarding the changes occurring in the operational state of the valve. The monitoring can in all cases be accomplished electrically so that it has no effect on the mechanical design of the manipulation system itself.

The present invention also concerns an apparatus for carrying out the procedure described above. This apparatus is characterized in that it comprises an integral system consisting of storage and treatment volumes and of conduits connecting these, wherein every conduit between two volumes contains at least one valve point communicating with a refrigerator and where the conduit may be cooled to be closed by the liquid within the conduit, and which has furthermore been provided with an electrically controllable heating element by means of which the valve is openable by raising its temperature to be higher than the freezing point of the liquid. It is possible to carry out the different embodiments of the system described, by appropriately developing and modifying the apparatus. For instance, with a view to abrupt cut-off of a liquid flow progressing in the system one may in the system use valves of which the cross section has been shaped so narrow in one dimension at least that the liquid arriving at the empty, pre-refrigerated valve will freeze instantaneously. It is further of advantage in view of the control and supervision of the system's operation to use electrical resistances as heating elements for the valves and to provide the valves and conduits with measuring circuits by the aid of which the treatment operations in various parts of the system may be continuously followed.

A particularly advantageous embodiment of the apparatus of the invention is characterized in that the valves have been formed by using components containing film resistances so that several valves belonging to the system have been established with the aid of one single component. Such valves have preferably very small size, whereby great numbers of such may be accommodated in a minimal space. Since on the other hand plate-shaped components containing resistances are inexpensive in their manufacture, the price does not either impose any restrictions on truly ample use of such valves. For instance, the price of one single valve will be only between 1/10 and 1/1000 (depending on size) of that of the equivalent magnetic valve. It is thus possible, using components which contain resistances, to construct even comparatively complex pieces of apparatus operating with small liquid batches to be built as compact units having no moving parts at all and operating exclusively on electrical control.

The establishing of valves in the conduits with the aid of a component containing resistances may be accomplished in practice in that the component is placed against a surface, whereby the valves will be formed between this surface and the resistances in the component. The other side of the components is in that case connected to the refrigerator, which can be kept at a temperature lower than the freezing point of the liquid under manipulation all the time. When now the gap remaining between the surface and the component is allowed to fill with liquid, the valve points are automatically formed opposite the resistances, while the spaces between resistances freeze up permanently.

A favourable embodiment of the apparatus of the invention is characterized in that the apparatus comprises at least one unit composed of storage or treatment volumes, wherein the volumes have been connected in parallel by connecting them with the aid of connecting conduits in between two parallel main lines and wherein each connecting conduit has been provided with a valve. Such a unit may be used for storage of liquid batches, and because the valves can be made extremely small in absence of moving parts, the units may be built as compact batteries of cells which may comprise truly great numbers of small storage volumes of mutually identical size. The apparatus may thus comprise a large sample register from which any desired liquid batch may be taken for treatment as desired. The units composed of storage volumes may be constructed e.g. in the shape of a rectangular parallelepipedon which contains both the storage volumes and the main lines and connecting conduits belonging thereto. The valves in parallel connecting conduits connecting with the same main line are in such a case with particular advantage formed with the aid of one single component containing film resistances. This simplifies the design of the apparatus appreciably, particularly when the number of storage volumes is very high. In practice, the valves may be carried out, for instance, by carrying the connecting conduits running within the block containing storage volumes, up to the surface of the block and by covering the apertures of the conduits by placing the component containing resistances upon them. The resistances will then constitute on the surface of the block the requisite flow passages connecting the apertures of the conduits and which can be open by means of an electric current passing through the resistances. The permanently frozen areas, again, effectively separate the flow passages belonging to different connecting conduits from each other.

The invention may further be applied so that the apparatus comprises, on the side of the unit composed of storage volumes, also volumes for dispensing and mixing liquid batches. The dispensing volumes may be arranged in a unit comprising parallel volumes provided with connecting conduits with valves and which are mutually of different size. It is moreover possible to connect such systems composed of parallel volumes in series, whereby the dispensing possibilities of the apparatus are even further increased. Since what is dispensed is usually liquid batches stored in the storage volumes, it is appropriate to dispose the dispensing unit beside the unit consisting of storage volumes, so that they have a common main line. Hereby the distance between storage volume and dispensing unit will be minimized. The purpose of the mixing volume comprised in the apparatus, again, is to enable various liquid batches to be combined in desired proportions. It is advantageous to place the mixing volume close to the dispensing unit, and in the transferring of the dispensed liquid batches to the mixing volume the same conduits may be used, in which case the liquid transferred last also flushes the conduits and dispensing volumes.

If the apparatus furthermore contains volumes for incubation of the mixed liquid batches, it may be used to accomplish the reactions taking place between the liquids. The incubation volumes may be arranged in parallel to constitute a battery unit consistent in its construction with the above-mentioned battery-type storage units. One may thus in connection with the incubation volumes use similar components containing film resistances, to form the valves in the connecting conduits.

In order that observations could be made concerning the reactions taking place in the incubation volumes, the apparatus has to comprise a separate detection volume, which is placed close to the incubation volumes. The detection volume may have a capacity so small that the liquid quantity which one has to transfer from the incubation volume to the detection volume is only a fraction of the total volume of the liquid mixture reacting in the incubation volume. It is then advantageous to proceed so that the liquid batch is removed from the detection volume immediately after the measurement has been made and for the next measurement taking place after a certain time interval, which may possibly depend on the result of detection, a new liquid sample is drawn from the incubation volume. Since furthermore the detection volume is easy to flush, one single detection volume may be used to observe simultaneously the progress of numerous separate reactions. The apparatus may therefore comprise a plurality of entities consisting of storage and dispensing units, mixing volumes and incubation units, which require jointly only one detection volume. Since the valves belonging to such an analysis apparatus can be electronically controlled, the operation of the apparatus is fully automatable.

The apparatus of the invention is particularly well suited for carrying out wet chemical analysis with small batches of liquid, and the invention may be applied particularly in clinical chemistry, as an electronically controllable analyzer operating without moving mechanical parts.

In clinical analysis, one or several components are determined from a great number of liquid samples and, furthermore, on the basis of the results repetitions and checks are often made, as well as supplementary measurements. The determination of each component incorporates several storing, dispensing, combining, mixing and separation operations to be performed with liquid batches, or more generally expressed it requires logic actions performed with liquids, and which have a very high need of automation.

Present-day microcomputers would not impose any obstacles in the way of programming the manipulation at that level of complexity on which the analytical or clinical chemist may operate by manual methods. However, in existing analytic equipment direct electric control cannot be applied in the handling of separate liquid batches, owing in the first place to the magnet valves which have large dead spaces and high unit costs. Therefore the quantitative and logic actions with regard to liquid batches are in the first place performed mechanically, either by transferring liquids continuously forward in parallel passage systems and by conducting them together in Tee connectors, that is without moving mechanical logics elements, or by mechanically moving separate containers or container coupled together, between which liquids are still transferred mechanically, by means of various kinds of pipettes, through the air. With the aid of such mechanical logics actions only the most central, frequently recurring steps in liquid manipulation can be carried out, even then mostly in a rigidly constant sequence.

In a separate system problems of reliability and accuracy, as well as many compromises, are caused by the numerous mechanical operations, and the quality of the analysis will correspondingly suffer. Furthermore, discardable separate products cause increased operating costs, for instance. In the continuous flow system, again the great problem is a high consumption of reagents and the errors caused by residues from preceding liquid batches in the treatment of the following liquid batches. To be successful, correction of these errors requires highly constant operating conditions and a remarkably large computer capacity. Any substantial reprogramming is impossible without structural changes, although on the other hand the operational logics consisting of a coherent system of passages and of continuous flow is known for its high reliability in service. It may be mentioned, furthermore, that both systems are sequential of their nature, that is, events follow rigidly one upon the other in a predetermined sequence. Parallel cases are only achievable by connecting several serial systems in parallel, whereby the bulk of the system increases, without any increase in flexibility.

The detectors belonging to the analysis equipment, such as the commonly employed optical detectors, may in theory operate on quite minimal liquid volumes, and it would be advantageous with a view both to the limited availability of sample material and to the consumption of reagents to restrict the requisite quantity of liquid to be as small as possible. In clinical chemistry, for instance, where the customary sample material is blood, numerous different tests have to be made on one sample. However, the accuracy of existing dispensing and manipulation systems does not, as a rule, allow to use any liquid quantities below the order of magnitude of one microliter.

Strictly speaking, existing automatic analyzers cannot even be considered automatic but merely mechanized, because it is usually not possible to implement the typical functions of automation: feedback, sefl-check or self-correction. These deficiencies are due to the limitations of the liquid manipulation systems. For the same reason it is for instance not possible to utilize the detectors efficiently, because in order to minimize the liquid operations the sample preempts the detector even when no measurement is being made. The greatest deficiency in present-day liquid manipulation systems is the lack of a storage and handling system which at the peak of logics technology, in modern computers, corresponds to the RAM (Random Access Memory). The desirable objects associated with automation of clinical liquid manipulation systems have been defined, for instance in the report by T. D. Kinney and R. S. Melville "Mechanization, automation and increased effectiveness of the clinic laboratory" (U.S. Department of Health, Education and Welfare, Publication No. (NIH) 78-145), where it is observed on pages 8-9 that the system should: "(1) produce accurate, precise and reproducible results; (2) have a capacity to perform several tests in sequence with a minimal delay of time between sample entry and result; (3) use small samples (25 microliters or less) per analysis; (4) provide if possible for the entry of emergency specimens into the system without interruption of ongoing analytic procedures; (5) still insure positive sample identification from input to output; (6) have mechanisms for error detection and methods for standardization; (7) have every step in an automated procedure monitored to detect any abnormal function; and (8) have reliability and minimal maintenance requirements designed into an instrument from the outset."

In the analyzer carried out as taught by the present invention the above-mentioned objects can be acheieved and the drawbacks of the apparatus of prior art can be avoided at the same time. This is based on the fact that the manipulation of liquid batches is based on their transferring with the aid of mere differential pressure without any moving parts. The transferring and other manipulation of the liquids is controlled directly electronically, and the supervision of liquid operations and of other manipulation also takes place electronically. It is therefore most advantageous to use a computer to control the analyzer, whereby storage, dispensing and other steps of manipulation can be programmed to take place automatically. The analyzer may moreover be continuously programmed, re-controlled and remote-controlled. The absence of moving parts increases the reliability of the analyzer and reduces its manufacturing cost. Since the liquid batches to be treated may be very small, the time utilisation of the detector can be made efficient and the running costs low. Owing to the same reason the storage volumes may be shaped into a sample register, which may contain even several thousand samples taken from patients. When the samples are water-based and their freezing points are very close together, the operation of the valves is easy to check and there is no objection to connecting them into one and the same refrigeration system if such is otherwise possible considering the construction of the analyzer. Any desired sample may be transferred from the register to treatment automatically and, if required, the results can be easily and rapidly checked by repeating the particular measurement.

The invention shall be described in the following in detail with the aid of examples, with reference to the attached drawings, wherein:

FIG. 1 presents the unit composed of storage volumes.

FIG. 2 shows the unit of FIG. 1, in top view.

FIG. 3 shows the section along line III—III in FIG. 2,

FIG. 4 shows the section along line IV—IV in FIG. 2,

FIG. 5 shows a plate-like component containing film resistances,

Figure 7:
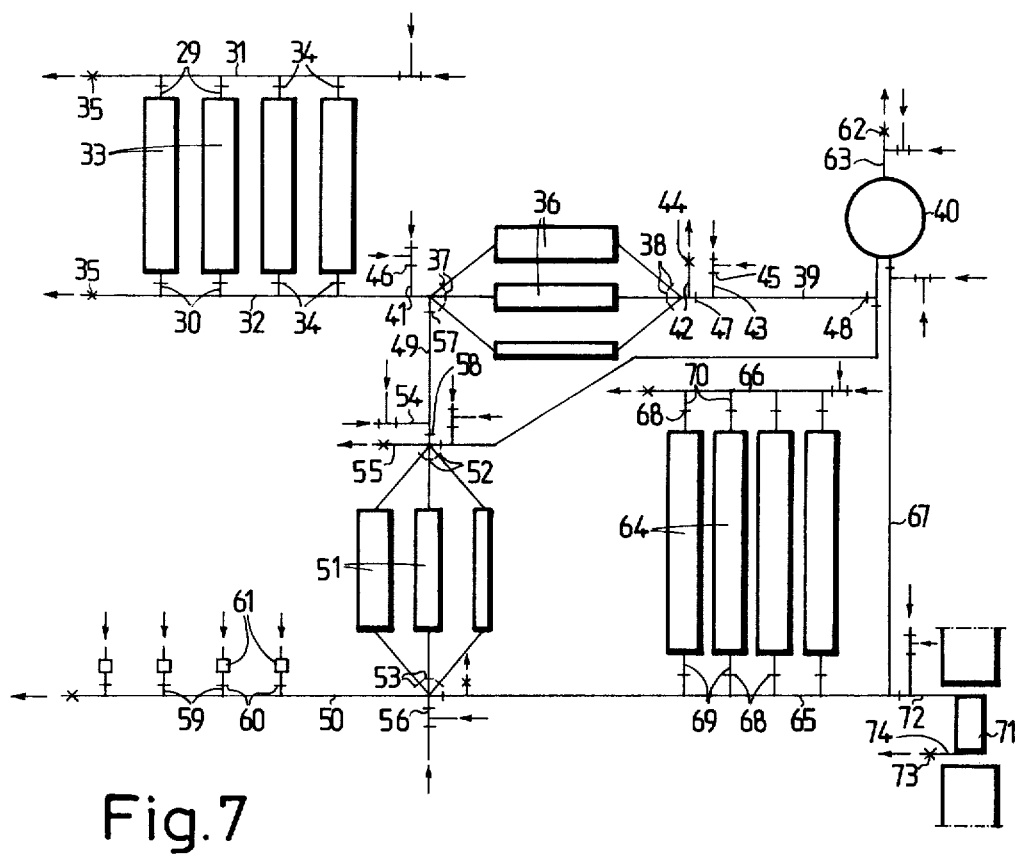

FIG. 6 shows, like FIG. 4, in section part of the unit composed by storage volumes and against the surface of which a component as shown in FIG. 5 has been placed, FIG. 7 is a schematic diagram of an analyzer according to the invention, consisting of volumes and of conduits with valves connecting them, and FIG. 8 is the diagram illustrating the performing of an RIA determination by the apparatus of the invention.

In FIG. 1, a block shaped like a rectangular parallelepipedon, 1, has been shown, which constitutes a battery-like unit comprising storage volumes 2. The storage volumes 2 belonging to this unit have been connected in parallel between two main lines by connecting their both ends through connecting conduits with valve to the said main lines. The ends of the storage volumes 2 are on the side 3 of the rectangular block 1, and the main lines of the volumes have been carried into the block through the side 4, the line ends 5,6 being visible in FIG. 1.

The construction of the block 1 of FIG. 1 is seen in greater detail in FIGS. 2-4. The storage volumes 2 are cylindrical and they extend from the side 3 of the block to the opposite side 7. The main lines of the volumes pass mainly in the interior of the block 1, adjacent and parallel to the sides 3 and 7. The parts parallel to the sides have been indicated in the drawings by reference numerals 8 and 9. At the end of parts 8 and 9, the main lines turn to parallell the storage volumes 2 and they rise to the surface of the block on the sides 3 and 7. The apertures on the side 3 belonging to the main line have been indicated in the drawings with 10 and 11. Numerals 12 and 13 indicate, further, apertures which by the ducts 14 and 15 communicate with the main line entry points 5 on the side 4 of the block. The other main line has been carried in on the side 7 of the block and connected to the entry points 6 in fully equivalent manner. Each one of the four cylindrical storage volumes 2 has been connected by both ends, by mediation of the connecting conduit 16,17, to the straight part 8,9 of the respective main line running within the block. Each connecting conduit 16,17 runs a short distance along the surface of the block 1, and the apertures on the side 3 belonging to the connecting conduits have been indicated with 18 and 19 in the drawing.

The block 1 of FIGS. 1–4 is not yet in itself operable as a unit for the storing of liquid batches. Thus, the ends of the storage volumes 2 opening on the sides 3 and 7 have to be tightly sealed so that the volumes communicate with the space external to the block 1 only by their narrow connecting and main conduits. Furthermore, each one of the connecting conduits 16,17 has to be fitted with a valve between the storage volume and the main line, by the aid of which the storage volume can be opened and closed. In order to form the valve points, the plate-like component 20 shown in FIG. 5 is used, which comprises rectangular, film-like electrical resistances 21. The resistances 21 have been connected in parallel between a common film-like conductor 22 and areas 23 coated with conductive material. The resistances may be any kind of material used in film resistors, for instance they may consists of a mixture of noble metal oxides, and the plate constituting the base for resistances and conductors in the component 20 may consist of aluminium oxide, for instance.

The forming of valves with the aid of the component 20 is accomplished by placing the component opposite the apertures 10–13, 18–19 on the side 3 of the block 1 so that the film resistances 21 cover the apertures grouped two and two. FIG. 6 displays one of the valves formed in this way of the connecting conduit 16. There is insulating material 24 between the component surface 20 and the surface 3, and opposite to the resistance 21 there has been mounted a separate transistor resistance 25 in such manner that a narrow passage 26 has been formed between these resistances. Against the bottom of the component 20, the cooler 27 has been placed, which can be continuously kept at a temperature lower than the freezing point of the liquids to be transferred through the connecting conduit 16. The lead 21 on the component, as well as the points 23 coated with conductive material have been connected over lead wires 28 to a voltage source. The leads of the thermistor resistance 25 have not been depicted in FIG. 6.

The component of FIG. 5 constitutes on the side 3 of the block 1, altogether six parallel valves, four of them belonging to the connecting conduits 16 and two to the main line of this side. A similar component is also placed on the opposite side 7 of the block.

The operation of the valve is based on temperature control in the passage 26 effected with the aid of the electrical resistance 21 and the cooler 27. The cooler 27 keeps the surroundings of the valve permanently at a temperature lower than the freezing point of the liquids to be transported in the connecting conduits 16. However, an electric current passing through the resistance 21 generates heat so that the passage 26 is kept open. If the electric current is switched off while the connecting conduit 16 is liquid-filled, the passage 26 will immediately freeze shut. On the other hand if the connecting conduit 16 is empty at the moment when the current is interrupted, the valve will remain open to gas flows, but it will freeze shut at once when a liquid flow arrives at the passage 26. Thus the valve has three functional positions: it may be fully closed, or open to gas flow, or open to both gas and liquid flow. The task of the thermistor resistance 25 is to monitor the operational state of the valve and to deliver a signal of the changes of state of aggregatiion taking place in the passage 26.

FIG. 7 illustrates an apparatus composed of conduits and of volumes connected thereto, intended for storage and analysis of batches of liquid. Small cross lines on the conduits represent valves carried out according to the principle shown in FIG. 6. Crosses indicate high power valves, which can be closed dynamically, that is, the precooled valve freezes shut immediately after the liquid has reached its site. The valves indicated by a single cross line, again, are low resistance valves intended to be closed while the liquid is stationary. The apparatus of the figure comprises a storage unit consisting of four storage volumes 33 connected by means of connecting conduits 29,30 between two parallel main lines 31,32, and in which unit the connecting conduits have been fitted with low resistance valves 34 and the main lines contain high power valves 35. This storage unit may be carried out as shown in FIGS. 1–6. The main line 32 of the storage unit connects with a dispensing unit, composed of parallel and mutually different sized volumes 36. Each volume 36 is separable by means of valves 37,38 from the other volumes belonging to the dispensing unit and from the main lines 32 and 39. The main line 39 connects the dispensing unit to the mixing volume 40 at the end opposite with reference to the said storage unit, and into which the quantity of stored liquid dispensed by the dispensing unit may be transferred. To the main lines 32 and 39 have further been connected auxiliary lines 41–43 lying on both sides of the dispensing unit and which enable an auxiliary liquid to be used in connection with dispensing. The auxiliary line 42 has been fitted with a high power valve 44, while the auxiliary lines 41 and 43 carry low resistance valves 45 and 46, behind which the lines branch into two parts. In the main line 39 furthermore two low resistance valves 47 and 48 have been installed.

Behind the dispensing unit constituted by the parallel volumes 36 there has been placed in the apparatus another dispensing unit of exactly equivalent design. This unit lies between two main lines 49 and 50 and it consists of three parallel, mutually different sized volumes 51 and of the valves 52 and 53. To the main lines 49 and 50, valve-equipped auxiliary lines 54–56 have been connected, and the line 49 furthermore contains two low resistance valves 57 and 58. Moreover connected with the main line 50 are four parallel entry lines 59, containing low resistance valves 60 and pressure-sensitive piezoresistive elements 61 delivering signals on the basis of which the transport of liquid batches in the lines may be controlled and guided. The liquid batches dispensed into the dispensing unit formed by the volumes 51 are intended to be transferred into the mixing volume 40, and this transfer is advantageously performed through the main lines 49 and 39 so that the liquid in question pushes ahead of itself into the mixing volume a liquid batch that has been dispensed before into any one of the volumes 36, whereby the dilution liquid passing last will perform the flushing of the lines and dispensing volumes. Further connected to the mixing volume 40 is the auxiliary line 63, provided with high power valve 62, by which dynamic closure of the mixing volume is accomplished.

The operation of the apparatus in the capacity of analyzer is based on the reactions taking place between the liquid batches conducted into the mixing volume 40 and on their observing, and to this end the apparatus comprises an incubation unit consisting of parallel incubation volumes 64. This unit is equivalent in its structure to the mentioned storing unit made up of the volumes 33, and thus it comprises two main lines 65 and 66, the first of these communicating by the line 67 with the mixing volume 40. The incubation volumes 64 have been connected by connecting conduits 69 and 70 fitted with low resistance valves, to said main lines. To the purpose of observing the reactions, there has been placed beside the incubation unit, a detection volume 71, which has a volume substantially smaller than the incubation volumes 64. The detection volume 71 communicates by the line 72 with the main line 65, and thereto has been connected a drain line 74 fitted with high power valve 73, through which line the detection volume is drained immediately after a measurement has been performed.

The transportation of the liquid batches in the apparatus of FIG. 7 is accomplished with the aid of differential pressure provided in the lines. The principle is then, that the valves on the desired transfer route are kept open with the aid of the electrical resistances, while all crossing lines have been closed. The liquid batch that is being transferred can be stopped at a high power valve by cooling the respective valve in advance, whereby it is at once frozen shut by the arriving liquid column. After this has taken place, the electric current may also be switched off another valve on the said transfer route and which is not liquid-filled, whereby the liquid will be incarcerated between these valves. When it is again desired to move the liquid forward, the valves are opened by thawing the ice plugs in them with the aid of electic current.

When performing with the apparatus the dispensing of two batches of liquid in the dispensing units consisting of the volumes 51 and 36 and the mixing of the batches of liquid and their dilution in the mixing volume 40, the first step is to clean the dispensing volumes and the lines 49 and 39, to which purpose one may use pure solvent of the kind incorporated in the liquid batches. For the part of the dispensing unit constituted by the volumes 36 this is accomplished in that through the line consisting of conduits 54, 49, 39 and 43 is conducted pure solvent and, after the lines and the volumes 36 have been sufficiently cleaned, the valves 57, 47 and 43 are closed. In this same connection one may with the aid of valves 37 and 38 permanently close those dispensing volumes which are not required in the dispensing process in hand. Thereafter, the valves 46 and 44 of the auxiliary lines 41 and 42 are opened and the solvent is drained from the volume 36 by conducting into this volume through the auxiliary lines, at first gas and a readily volatile exchange fluid, and finally mere dry gas until the volume has dried out. The adequacy of drying may be tested by means of the valve 44 by de-energizing it. If then freezing occurs at this valve, which is observed as a reduction of gas flow, the drying has to be continued. The cleaning, flushing and drying of volumes 59 and 40 may be accomplished in fully identical way. The filling of volume 36 with liquid stored in any one of the volumes 33, whereby this liquid will be a component in the mixture that is established, is carried out through the main line 32. After the volume 36 has been filled to capacity, the liquid flow arrives at the high power valve 44 in the auxiliary line 42, and this valve immediately closes. Hereafter the valve 34 in the connecting conduit of the respective storage volume is also closed. Filling of the volume 51 with another mixture component is similarly accomplished with the aid of auxiliary lines 56 and 55. At this stage the components of the mixture to be formed are enclosed in the volumes 51 and 36, and the lines 49 and 39, as well as valves 60, 58, 57, 47, and 48 are filled with solvent. Wet performs thereafter the transfer of the liquid batches in volumes 51 and 36 into the empty mixing volume 40 with the aid of pure solvent brought in through the lines 59 and 50. To accomplish this, the said valves, closed with the aid of solvent, are opened, whereby the solvent will pushed the liquid batches ahead into the volume 40. Thereby the solvent will flush the liquids dispensed into volumes 51 and 36, quantitatively, into the volume 40, and as it finally fills this volume it carries out the dilution of the mixture to desired volume. The volume 40 closes off as the mixture arrives at the valve 62. The error due to filling of this valve in different degrees is minor because this valve has a minimal volume compared with the large capacity of the volume 40.

The procedure and apparatus for manipulating batches of liquid of the present invention may be applied in connection with various kinds of analytic methods, independent of the mode of operation of the detector. For instance, the radio-immunological assay (RIA) based on radioactivity may be carried out in the manner illustrated by FIG. 8. This figure presents schematically the most important functional units of the analysis apparatus. The samples, standards and reagents are stored in registers 75-77, which communicate through the dispensing units 78 and 79 with the dilution unit 80 which the method implies. The dilution unit may comprise e.g. a mixer and thereto attached a dispenser, which is filled from the mixer to the capacity implied by the dilution flushing, for instance ⅔ of the liquid batch contained in the mixer are transferred into the dispenser, which is in its turn emptied into one of the incubation volumes in the register 81. The one-third which has remained in the mixer is further diluted by filling the mixer with the respective reagent and emptying the dispenser as before. In this way it is accomplished that a dilution series 1:3 is transferred from the sample register 75 to incubation register 81. It is thus understood that the diluting ratio can be chosen with full freedom, with the aid of the emptying proportion.

Incubation takes place in conventional manner, and in its course part of the radioactivity becomes bound to one of the participating components. The bound and soluble fractions are separated in the separator 82, the functioning of which may be based e.g. on the binding of magnetic particles electromagnetically to be stationary at the separation station for the duration of washing out the soluble fraction, whereupon the particles may be transferred with a small liquid quantity directly to the detector 83, of which there may be several.

The bound fraction—most often the object of measurement in an apparatus according to the invention—is easy to concentrate to such small bulk that a gamma radiation semiconductor detector may be used as detector. This type of detector is not usable in conventional counters, in which test tubes etc. are mechanically moved, owing to the large volume.

The control electronics, such as a microcomputer for instance, has been indicated with the reference numeral 84 in the figures. The automatic RIA apparatus depicted here can be programmed to perform all those controls, checks and standardisations which the person making the determination would otherwise have to do manually, on having obtained test results which imply such measures. This is because in this apparatus all reagents, even those rarely needed, are automatically available.

It is obvious to a person skilled in the art that different embodiments of the invention are not confined to the preceding examples, but that they may vary within the scope of the claims following below. For instance, in the apparatus presented in FIG. 7 there have only been included examples of those most typical treatment units which may come into question when the present invention is applied in practice.

I claim:

1. An apparatus for the treatment of batches of liquid comprising: a number of storage or treatment chambers, and a network of conduits associated therewith, wherein: said chambers are placed within said network enabling the conduits to provide connections between the chambers and each connection between two chambers comprises at least one valve point communicating with a refrigerator and being formed with a conduit subject to being frozen shut by means of liquid, and said apparatus being further provided with an electrically controllable heating element, whereby the valve is caused to open by raising its temperature to a level higher than the freezing point of the liquid.

2. An apparatus according to claim 1, comprising: valve points having a cross section shaped to be sufficiently narrow in at least one dimension as that liquid arriving at the empty valve being cooled to a temperature lower than the freezing point of the liquid immediately freezes and blocks the line.

3. An apparatus according to claim 2, wherein: a flow or differential pressure measuring circuit is connected to the lines, by the aid of which, transfer of batches of liquid in the apparatus are observed.

4. An apparatus according to claim 1, wherein: said heating elements of the valves are electrical resistances and said valves are connected into measuring circuits whereby operation can be observed.

5. An apparatus according to claim 4, wherein: said valves are formed with component means having film resistance whereby, a plurality of valves are defined by one single component.

6. An apparatus according to claim 5, wherein: said component means containing film resistances is against a surface so that the valves are formed in the intervals between said surface and the resistances on the component, and another side of the component is connected to a refrigerator maintained continuously at a temperature below the freezinfg point of the liquid that is being treated.

7. An apparatus according to claim 1, wherein: said apparatus comprises at least one unit formed of storage or treatment chambers and the chambers are connected in parallel through connecting conduits between two parallel main lines and providing each of the connecting conduits with a valve.

8. An apparatus according to claim 7, wherein: the valves in parallel connecting conduits connected to one and the same main line are formed with one component containing film resistances.

9. A process for the treatment of batches of liquid by means of an apparatus constituted by a number of chambers and a network of conduits, the chambers being placed within said network whereby said conduits provide connections between the chambers and each respective connection between two chambers has at least one section connected with a refrigerator and provided with an electrically controllable heating element, each of said respective sections having the function of a regulatable valve, and said process comprises the steps of:
   introducing a batch of liquid into a part of said apparatus;
   transferring said batch into a selected chamber by regulating the temperature of the valves in the conduits along which the batch is to travel at a level above the freezing point of the liquid and by moving the batch through said conduits into said chamber by means of a pressure difference;
   holding the batch in said chamber for storage or treatment by closing at least one of the valves in the conduits in communication with said chamber by means of liquid freezing after the heating element in the valve has been switched off; and
   removing said batch from the chamber after the storage or treatment by regulating the temperature of the valves in the conduits along which the batch is to be removed, above the freezing point of the liquid and applying a pressure difference into said conduits.

10. A process according to claim 9, comprising the steps of: monitoring the transfer of the batch of liquid in the apparatus by means of flow or differential pressure measuring circuit connected to the conduits.

11. A process according to claim 9, comprising the steps of: monitoring the operation of the valves by means of operational state measuring circuits being connected thereto.

12. A process according to claim 11, comprising steps of: cooling a closing conduit valve having an electrical resistance as a heating element, by interrupting electric current passing through the resistance; and monitoring the operational state of said valve by a thermistor of the resistance.

* * * * *